United States Patent [19]
Rattenborg et al.

[11] 4,068,096
[45] Jan. 10, 1978

[54] PRESSURE MONITORING SYSTEM
[75] Inventors: Christen C. Rattenborg, Chicago; Raymond J. Mikula, Evanston, both of Ill.
[73] Assignee: Continental IL National Bank and Trust Co., Chicago, Ill.
[21] Appl. No.: 696,579
[22] Filed: June 16, 1976
[51] Int. Cl.² .......................................... H04M 11/04
[52] U.S. Cl. .................................. 179/2 A; 128/2.1 A
[58] Field of Search ................... 179/2 R, 2 A, 2 DP, 179/5 R; 340/189 M, 20 TR; 128/2.1 A, 2.06 R, 2.08

[56] References Cited
U.S. PATENT DOCUMENTS

| 3,426,150 | 2/1969 | Tygart | 128/2.1 A |
| 3,726,270 | 4/1973 | Griffis | 128/2.1 A |
| 3,848,591 | 11/1974 | Smythe | 128/2.08 |

OTHER PUBLICATIONS
Bell Laboratories Record, "Electrocardiograms by Telephones," Feb. 1966 issue, pp. 43–47.

Primary Examiner—William C. Cooper
Assistant Examiner—Joseph A. Popek
Attorney, Agent, or Firm—Lockwood, Dewey, Zickert & Alex

[57] ABSTRACT

A system for monitoring respiratory pressure or other pressure-variable function at a remote location develops within a transmitter terminal a carrier tone frequency-modulated according to applied pressure. The carrier tone is conveyed over a conventional telephone channel to a receiver terminal wherein an analog signal is developed from the carrier tone for application to recording or indicating instruments. The base frequency and deviation characteristic of the carrier tone is preset and non-user adjustable to avoid the necessity of setting up the system prior to use. To assure system continuity a pilot tone is generated at the receiver terminal and conveyed over the telephone channel to the transmitter terminal, and an alarm is sounded at the terminals when either but not both of the pilot and carrier tones are absent in the telephone channel. The terminals are preferably constructed within compact housings having wells for receiving the handsets of associated telephones for convenience of use.

4 Claims, 4 Drawing Figures

PRESSURE MONITORING SYSTEM

BACKGROUND OF THE INVENTION

The present invention is directed to pressure surveillance systems, and more particularly to a system for monitoring a pressure-variable biological function such as respiratory pressure at a remote location. The system is particularly useful in monitoring the operation of a ventilator or similar forced-breathing type apparatus.

It is frequently desirable to monitor at a central location one or more pressure-variable biological functions of a patient located at a remote location. This situation arises in large hospitals where a patient located in a general care area must be given special treatment by apparatus requiring continuous or periodic monitoring by specialists at another location in the hospital, or at a nursing home or personal residence where such apparatus must be monitored at a distant hospital or clinic. One treatment frequently administered under these conditions involves the use of forced-breathing or ventilator apparatus, which assist the patient's lungs in maintaining normal breathing. To insure the proper operation of this apparatus it is necessary that the pressure level between the patient and the ventilator be periodically monitored. By analyzing variations in this pressure level the attending physician can ascertain not only that the ventilator is operating properly, but also the condition of the patient's respiratory system. Other pressure-variable biological parameters which can be monitored in this way include spontaneous breathing as measured by a pneumograph, arterial blood pressure, pulmonary functions, and intracranial pressure.

Heretofore, pressure-variable biological functions have been difficult to monitor because of the lack of a suitable transmission medium between the remote patient location and the central monitoring location. While existing telephone lines provide the greatest flexibility as a transmission medium, systems heretofore devised for transmitting pressure-variable biological data on a frequency-modulated carrier tone over such lines utilized laboratory-type equipment for generating the tone, which required a complicated and time-consuming set-up and adjustment prior to each use, and laboratory-type pressure transducers, which were sensitive to shock and temperature variations. Since the environment in which the patient is undergoing treatment is often not conducive to making precise time-consuming adjustments, and since the personnel operating the equipment may not be trained in making such adjustments or may not have sufficient time in the case of an emergency condition, such systems based on laboratory-type equipment have not proven practical for every-day use.

Accordingly, it is a general object of the present invention to provide a new and improved monitoring system for pressure-related biological functions which allows such functions to be monitored over ordinary telephone lines or other audio transmission channels at a location remotely located from the patient.

It is another object of the present invention to provide a new and improved monitoring system for pressure-variable biological functions which does not require adjustment prior to use.

It is another object of the present invention to provide a new and improved monitoring system for pressure-variable biological functions which includes alarm protection against failure of the transmission channel or system components.

It is another object of the present invention to provide a new and improved monitoring system for pressure-variable biological functions which can be utilized in conjunction with ordinary telephone equipment without direct connection thereto or modification thereof.

SUMMARY OF THE INVENTION

The invention is directed to a system for monitoring over an audio transmission channel at a first location a pressure-variable condition existing at a second location. The system incudes at the first location a transducer responsive to the pressure condition for generating an output signal having a voltage level related to the pressure, voltage-controlled generator means responsive to the output signal for generating a modulated carrier having a predetermined non-user adjustable base characteristic, and a fixed non-user adjustable deviation characteristic related to the voltage level of the output signal, and first interface means for applying the carrier to the transmission channel. The system includes at the first location second interface means for deriving the carrier from the transmission channel, demodulating means for developing from the derived carrier an analog signal having a predetermined non-user adjustable relationship to the deviation of the carrier from the base characteristic, and means for amplifying the analog signal to develop an output signal for application to indicating or recording means.

The system is further directed, in the above system, to the improvement wherein the system includes a pilot tone generator at the first location, the second interface means applying the pilot tone generated by the generator to the transmission channel, a pilot tone detector at the second location, the first interface means deriving the pilot tone from the transmission channel and applying the tone to the pilot tone detector, and alarm means responsive to the output of the pilot tone detector for generating an alarm in the absence of the pilot tone.

The invention is further directed to a ventilator surveillance system for monitoring at one location the pressure condition of a ventilator at a remote location. The system comprises a telephone line with handsets having earpieces and mouthpieces at both locations, means at the ventilator location for converting the pressure condition into an electrical signal and the electrical signal into an audio signal for transmission along the telephone line, means at the monitoring location for converting the audio signal to an electrical signal for application to an external readout of the pressure condition, means at both locations for interconnecting the earpieces and mouthpieces of the handsets to the audio signal, and means at one of the locations for monitoring the interconnection of the earpieces and mouthpieces to the audio signal and for energizing an alarm when the interconnection is broken.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
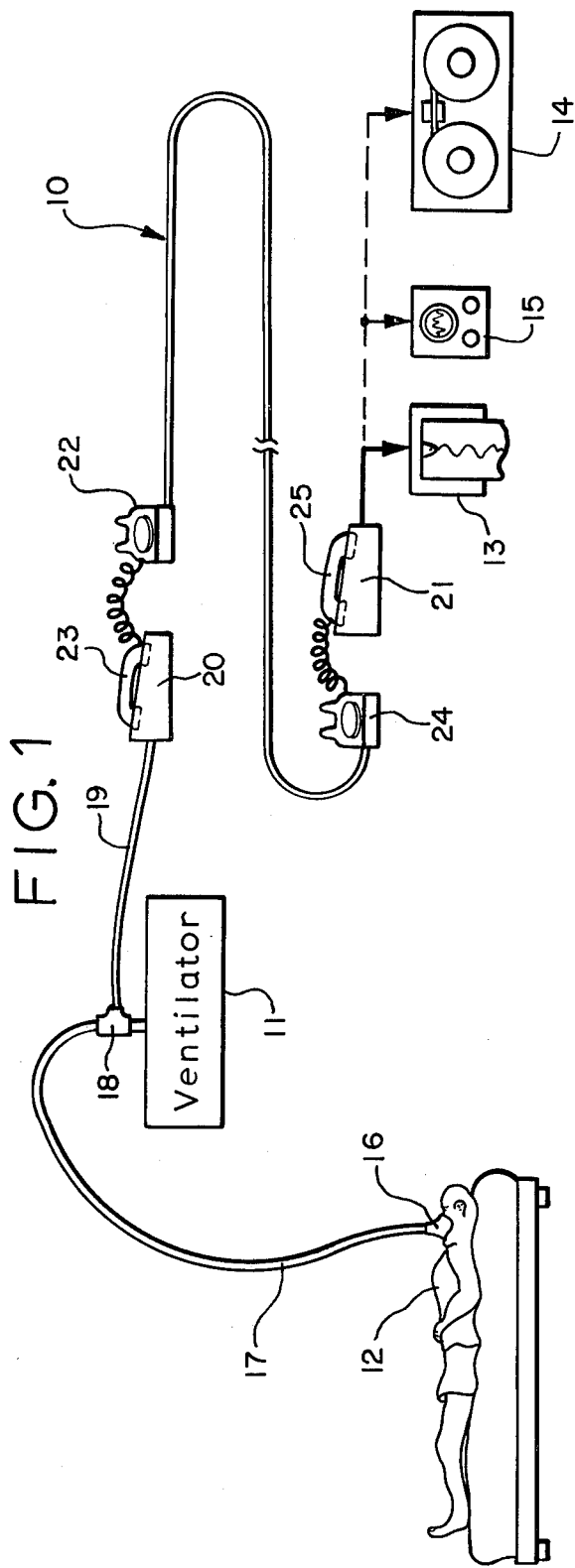
FIG. 1 is a diagrammatic presentation partially in functional block form useful in explaining the functioning of the monitoring system of the invention.

Referring to the Figures, and particularly to FIG. 1, a monitoring system 10 constructed in accordance with the present invention provides a data link between ventilator apparatus 11 being utilized to treat a patient 12 and a data recording or display device such as a strip chart 13, a tape recorder 14, or a display-type oscilloscope 15 located at a central monitoring location. In the particular application illustrated the breathing of the patient is being assisted by the ventilator apparatus 11, which may be conventional in design and construction and which may include a face mask 16 fitted to the patient and a conduit 17 between the face mask and the ventilator to provide a communicating air passageway between the ventilator and the patient. A monitoring capability for pressure in this passageway is provided by a T-connector 18 disposed along conduit 17 and a second conduit 19 which connects with the monitoring system 10.

The monitoring system includes, in accordance with the invention, a transmitter terminal 20 to which the pressure-sensing conduit 19 is connected, and a receiver terminal 21 to which the various recording or display devices 13-15 are connected. In accordance with one aspect of the invention, the transmitter terminal 20 is utilized in conjunction with a conventional telephone set 22 having a handset 23 positioned on the transmitter housing, and the receiver terminal 21 is utilized in conjunction with a conventional telephone set 24 having a handset 25 positioned on the receiver terminal housing. The telephone sets 22 and 24 are connected in a conventional manner by a transmission path 26, which is understood to include the usual switching and amplification circuitry necessary for voice transmission.

Figure 2:
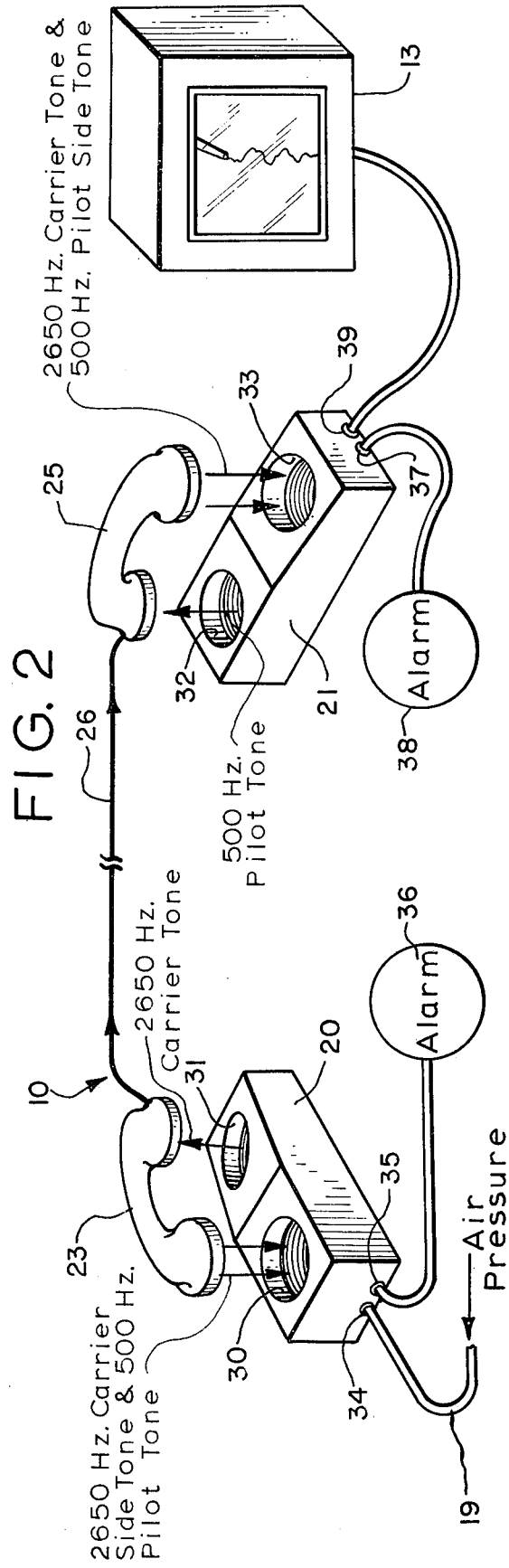
FIG. 2 is a perspective view of the receiver and transmitter terminals of the system.

Referring to FIG. 2, the transmitter and receiver terminals 20 and 21 are preferably constructed within compact housings suitable for table or desktop mounting. The transmitter terminal housing preferably includes a pair of transducer wells 30 and 31 for receiving the mouthpiece and earpiece of handset 23, and the housing of the receiver terminal 21 preferably includes a pair of transducer wells 32 and 33 for receiving the mouthpiece and earpiece of handset 25. When the handsets are positioned with their respective mouthpieces and earpieces seated in the respective transducer wells a high degree of sound coupling is obtained between the respective elements of the handset and the respective terminals.

As can best be seen in FIG. 2, the transmitter terminal 20 includes a fitting 34 for receiving the pressure sensing conduit 19, and an electrical fitting 35 for connection to an optical external alarm 36 for indicating failure of the system or interruption of its communication link. The external alarm may take the form of a wall or desk mounted buzzer, bell or light, depending on the environment in which the terminal is used, and will ordinarily supplement an internal alarm provided within the terminal for the same purpose. In the case of the receiver terminal 21, a similar connector 37 is provided for connection to an optional external alarm 38 which, like alarm 36, may be either a wall or desk-mounted light, buzzer or bell provided to supplement an internal alarm contained within the terminal. An additional electrical connector 39 is provided for connection to external recording or indicating instruments, such as the strip recorder 13 illustrated.

In operation, the transmitter terminal 20 generates a frequency-modulated 2650 Hz. carrier tone representative of the pressure level at fitting 34 and applies this to the mouthpiece of handset 23. At the same time, the receiver terminal 21 applies a 500 Hz. pilot tone to the mouthpiece of handset 25. The 500 Hz. pilot tone is conveyed to the transmitter terminal and applied thereto through the earpiece of handset 23, together with a 2650 Hz. side-tone generated in a conventional manner within telephone instrument 22 from the 2650 Hz. carrier tone applied to the mouthpiece of handset 23. The 2650 Hz. carrier tone is conveyed through channel 26 to the receiver terminal where it is applied, together with a 500 Hz. side-tone developed in a conventional manner within telephone instrument 24 from the 500 Hz. pilot tone applied to the mouthpiece of handset 25, to the input transducer of the receiver terminal. In the absence of one, but not both of the tones at the input transducer of either terminal an alarm is sounded to guard against failure of the telephone link or the system components. Since the alarm does not sound when both tones are absent, the alarm does not sound when the telephone is being used for voice communication prior to or following data transmission.

Figure 3:
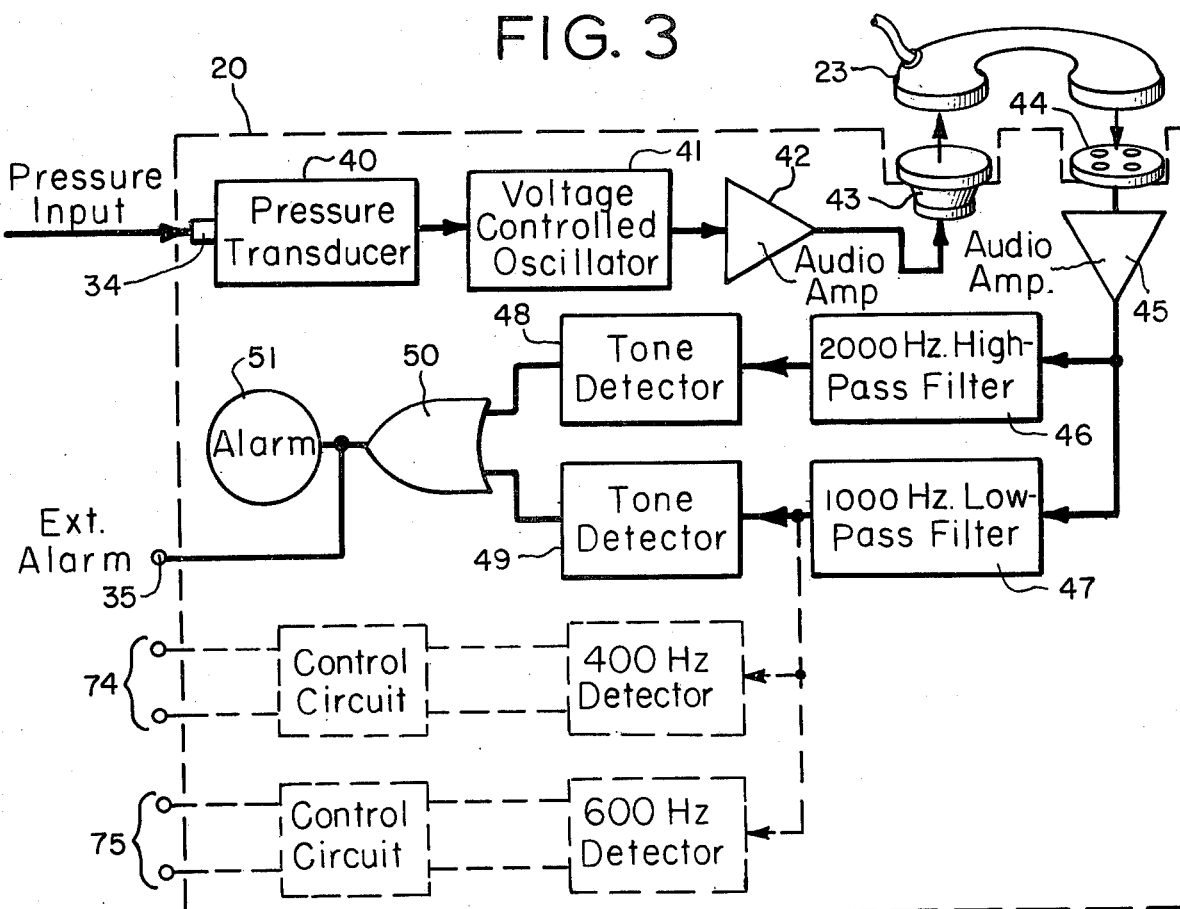
FIG. 3 is a functional block diagram of the transmitter terminal of the system.

Referring to FIG. 3, within transmitter terminal 20 the pressure developed by the ventilator or other function being monitored is applied to a pressure transducer 40. This transducer, which may be similar to the National Semiconductor (brand name) LX-3700 series, and otherwise conventional in design and construction, provides an output voltage proportional to the pressure applied to fitting 34. The transducer preferably includes integral temperature and voltage compensation such that the output has a high degree of proportionality to the applied pressure.

The output voltage developed by pressure transducer 40 is applied to a voltage-controlled oscillator 41 wherein an audio-frequency carrier tone is developed which has a frequency dependent on the applied voltage, and hence on the pressure applied to fitting 34. In practice, the frequency of the carrier tone developed by oscillator 41 decreases with increasing pressure, decreasing from a frequency of 2650 Hz in the absence of an applied pressure to a frequency of 2400 Hz upon application of a pressure of 70cm $H_2O$. In practice the applied pressures may range from +70cm $H_2O$ to −20cm $H_2O$, with corresponding shifts in carrier frequency resulting. The frequency-modulated carrier tone is amplified in a conventional audio amplifier stage 42 and applied to an output transducer 43, which functions as a miniature speaker to develop a sound signal for application to the mouthpiece of handset 23.

The 500 Hz pilot tone developed at the receiver terminal and transmitted upline to the transmitter terminal, and the side-tone of the 2650 Hz frequency-modulated carrier developed in the earpiece of handset 23, are received by an input transducer 44, which functions as a microphone to develop an audio frequency output signal. This output signal is applied to an audio amplifier 45 of conventional design wherein it is amplified. The amplified signal is then applied to a 2000 Hz high pass filter 46 and a 1000 Hz low pass filter 47. The output of filter 46 is applied to a first tone detector 48, which senses the presence of the 2650 Hz carrier tone, and the output of filter 47 is applied to a second tone detector 49, which senses the presence of the 500 Hz pilot tone. The outputs of the tone detectors are applied to an EXCLUSIVE OR gate 50, which in the absence of outputs from one, but not both, tone detectors produces an output signal. This signal is utilized to actuate an internal alarm 51 and, by way of connector 35, an optional external alarm 36.

Figure 4:
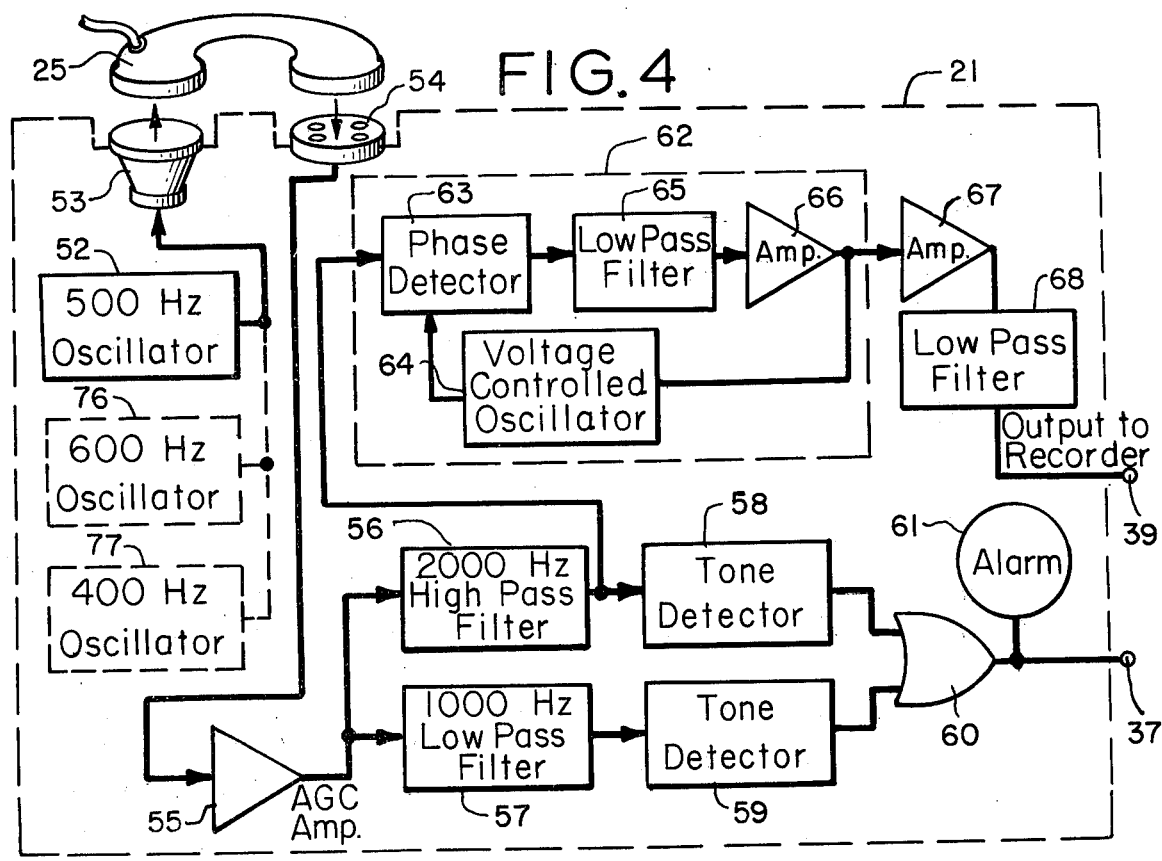
FIG. 4 is a functional block diagram of the receiver terminal of the monitoring system.

Referring to FIG. 4, the 500 Hz pilot tone is generated within the receiver terminal 21 by means of an oscillator 52. The output of this oscillator is applied to an output transducer 53 which functions as a miniature speaker to produce a 500 Hz sound signal for application to the mouthpiece of handset 25. Simultaneously, the 2650 Hz carrier tone developed by transmitter terminal 20 is applied, together with the 500 Hz side-tone generated within telephone instrument 22, to an input transducer 54 and converted to an audio signal which is applied to an audio amplifier 55. This amplifier, which is preferably of the automatic gain-controlled (AGC) type, develops an amplified audio signal which is applied to a 2000 Hz high pass filter 56 and a 1000 Hz low pass filter 57. The output of the 2000 Hz high pass filter 56 is applied to a tone detector 58, which senses the presence of the 2650 Hz frequency-modulated carrier tone. The output of the 1000 Hz low pass filter 57 is applied to a tone detector 59, which senses the presence of the 500 Hz pilot tone. The outputs of tone detectors 58 and 59 are applied to an EXCLUSIVE OR gate 60, which generates an output in the absence of one, but not both of the 500 Hz pilot and 2650 Hz frequency-modulated carrier tones. The output from EXCLUSIVE OR gate 60 triggers an internal alarm 61 and, by means of connector 37, an optional external alarm 36.

Typically, the maximum deviation of the frequency-modulated carrier tone is approximately 500 Hz from its 2650 Hz base frequency, and the tone detector is designed to respond to applied frequencies extending from 2000 Hz to 3000 Hz to assure continuous sensing of the carrier tone even at maximum deviation. The high pass filter 56, the low pass filter 57, and the tone detectors 58 and 59 may be commercially available components of a type readily available in integrated circuit form.

To develop an analog signal suitable for application to an indicator or reproducer, the amplified frequency-modulated carrier tone at the output of high pass filter 56 is applied to a phase-locked loop 62, which may be conventional in design and of a type readily available in integrated circuit form. Within the phase-locked loop a phase detector 63 compares the phase of the applied carrier tone with that of a second signal generated by an internal voltage controlled oscillator 64 to develop a control signal. This control signal is applied through a low pass filter 65 and amplifier 66 back to the voltage-controlled oscillator 64, which is designed to have a base frequency in the absence of an applied correction voltage equal to that of the voltage controlled oscillator 41 in transmitter terminal 20. As a result, an output voltage is developed at the output of amplifier 66 which is directly proportional to the deviation of the applied frequency-modulated carrier tone from its base frequency.

The analog output signal developed by the phase-locked loop 62 is amplified in a DC amplifier 67 and applied through a low pass filter 68 to connector 39, through which it is applied to the indicator or recorder being utilized. Filter 68 assures that the higher frequency pilot or carrier tones will be applied to the recorders.

In many applications it is desirable that provision be made in the monitoring system for adjusting the operation of the apparatus being monitored, or for communicating with attending medical personnel. To this end, the additional circuitry shown in broken lines in FIGS. 3 and 4 may be incorporated to provide separate control functions for an associated apparatus. Specifically, in the receiver terminal illustrated in FIG. 3, the output of the low pass filter 47, in addition to being applied to the pilot tone detector 49, is applied to 400 Hz and 600 Hz narrow-band tone detectors 70 and 71. These detectors, which are commercially available in integrated circuit form, produce an output in the presence of a tone at their respective detection frequencies. The outputs of the control tone detectors are coupled to respective control circuits 72 and 73, which initiate a contact closure across respective pairs of terminals 74 and 75 upon receipt of a tone. The contact closure may be utilized to control the functioning of an operating parameter in an associated apparatus, such as the breathing rate of a ventilator. It is contemplated that only one of the 400 Hz, 500 Hz or 600 Hz tones need be present at one time, since the bandwidth of the pilot tone detector 49 will allow the 400 Hz and 600 Hz control tones to be sensed as a pilot tone to assure system continuity.

The 400 Hz and 600 Hz control tones required for the control function are preferably generated within receiver terminal 21 by means of additional fixed-frequency oscillators 76 and 77, shown in broken lines in FIG. 4. It will be understood that these tones could also be generated by varying the operating frequency of the 500 Hz pilot tone generator 52 by means of suitable control circuitry. In any case, the control function is an optional feature of the invention to be provided where additional control functions are required, and the presence or absence of these control functions has no effect on the operation of the monitoring system. It will also be appreciated that additional control functions may be provided by providing additional control frequencies. The only limiting factor in this respect is the bandwidth of the various filters and the telephone transmission line.

By reason of its compactness and freedom from set-up procedures, the system of the invention lends itself to critical monitoring applications wherein a pressure-variable biological function must be accurately monitored at a remote location. The system requires only a standard voice-grade channel, allowing it to be used with ordinary telephone or radio circuits. The system can be utilized within a hospital for transmission of vital data to a central intensive care unit, or in the field where the diagnosis of a particular pressure-variable biological function must be undertaken without the presence of a physician.

To condition the system for use all that is necessary is to dial up the desired telephone number and once contact has been established, to seat the telephone handsets in the sockets of the respective terminals. Upon completion of the taking or receiving of data, either side may lift its handset away from the terminal and the alarm will automatically sound at the other terminal, either reminding the operator there to hand up the telephone, or causing the operator to pick up the telephone for instructions.

An additional modification contemplated for the terminal units is the provision of an automatic answering feature whereby either the transmitter terminal or receiver terminal may be called directly, without the intervention of an operator. This would be particularly desirable where either the central monitoring station or the data collection station must be left unattended for periods of time. Since the circuitry for such automated answering of a telephone is well known to the art, further explanation need not be given here.

Thus, a novel system has been described for transmitting pressure-variable biological data which is convenient to use and requires no initial set-up. The system includes a novel alarm arrangement which prevents inadvertent interruption of data because of either failure of the system or its communication link. The system may be inexpensively constructed of commercially available components, many of which are available in integrated circuit form for greater compactness and reliability.

It is contemplated that various modifications can be made to the system, such as the use of a pulse-width modulated carrier instead of a frequency-modulated carrier, and the use of other telephone coupling arrangements. Furthermore, other types of transmission channels may be utilized, such as radio links or dedicated audio lines. Also, it is contemplated that additional control circuitry may be provided in the transmitter terminal to automatically interrupt the carrier tone generated therein to sound an alarm at the receiver terminal upon occurrence of an event, such as failure of treatment apparatus, and it is further contemplated that additional control circuitry may be provided in the receiver terminal to automatically interrupt the pilot tone generated therein to sound an alarm at the transmitter terminal upon occurrence of an event at that end, such as failure of a recording instrument.

While particular embodiments of the invention have been shown and described, it will be obvious to those skilled in the art that changes and modifications may be made without departing from the invention in its broader aspects, and, therefore, the aim in the appended claims is to cover all such changes and modifications and fall within the true spirit and scope of the invention.

We claim:

1. A system for monitoring over an audio transmission channel at a first location a pressure-variable condition existing at a second location, said system comprising, in combination:

means including a transducer at said second location responsive to said pressure condition for generating within a predetermined frequency band a frequency-modulated output signal indicative of said pressure-variable condition;

first output coupling means at said second location for applying said frequency-modulated output signal to said transmission channel;

pilot tone generating means at said first location for generating a continuous pilot signal outside of said predetermined frequency range;

second output coupling means at said first location for applying said pilot signal to said transmission channel;

first input coupling means at said first location for deriving said frequency-modulated output signal and said pilot tone signal from said transmission channel;

demodulating means at said first location for developing from said derived output signal an analog output signal indicative of said pressure-variable condition;

first alarm means at said first location responsive to said derived pilot tone signal for generating an alarm in the absence of said pilot tone signal;

second input coupling means at said second location for deriving said pilot tone from said transmission channel; and second alarm means at said second location responsive to said derived pilot tone signal for generating an alarm at said second location in the absence of said pilot tone.

2. A monitoring system as defined in claim 1 wherein said transmission channel comprises a telephone system terminating in handsets at either end, said handsets each having an earphone and a microphone and providing a side-tone, and wherein said first and second output coupling means comprise transducers in communication with respective ones of said microphones, and wherein said first and second input coupling means comprise transducers in communication with respective ones of said ear phones.

3. A monitoring system as defined in claim 1 wherein said second input coupling means further derives said frequency-modulated output signal from said transmission channel, and wherein said second alarm means generate an alarm at said second location in the absence of said output signal.

4. A monitoring system as defined in claim 3 wherein said first alarm means generate an alarm at said first location in the absence of said output signal.

* * * * *